(12) United States Patent
Van Erlach (10) Patent No.: US 9,005,101 B1
(45) Date of Patent: Apr. 14, 2015

(54) SMART SURFACE BIOLOGICAL SENSOR AND THERAPY ADMINISTRATION

(71) Applicant: Julian Van Erlach, Dallas, TX (US)

(72) Inventor: Julian Van Erlach, Dallas, TX (US)

(*) Notice: Subject to any disclaimer, the term of this patent is extended or adjusted under 35 U.S.C. 154(b) by 0 days.

(21) Appl. No.: 14/461,862

(22) Filed: Aug. 18, 2014

Related U.S. Application Data (60) Provisional application No. 61/964,372, filed on Jan. 4, 2014.

(51) Int. Cl.
| | | |
|---|---|---|
| *A61N 2/00* | (2006.01) | |
| *A61B 17/22* | (2006.01) | |
| *A61N 5/06* | (2006.01) | |
| *A61N 5/00* | (2006.01) | |
| *A61F 7/08* | (2006.01) | |
| *A61N 7/00* | (2006.01) | |
| *A61H 23/00* | (2006.01) | |
| *A61N 1/36* | (2006.01) | |
| *A61N 1/372* | (2006.01) | |
| *A61M 5/172* | (2006.01) | |
| *A61B 5/00* | (2006.01) | |
| *A61N 5/067* | (2006.01) | |

(52) U.S. Cl.
CPC ............ *A61B 17/22004* (2013.01); *A61N 5/06* (2013.01); *A61N 5/00* (2013.01); *A61F 7/08* (2013.01); *A61N 7/00* (2013.01); *A61H 23/00* (2013.01); *A61N 1/36014* (2013.01); *A61N 1/37252* (2013.01); *A61M 5/1723* (2013.01); *A61N 2/002* (2013.01); *A61N 2005/067* (2013.01); *A61B 5/6892* (2013.01)

(58) Field of Classification Search
CPC ... A61M 21/00–21/02; A61G 7/057–7/05776; A61G 2007/05784–2007/05792; A47C 27/08–27/10; A61B 5/447; A61B 5/6892

USPC ............................ 607/6–7; 600/9–15, 26–28
See application file for complete search history.

(56) References Cited

U.S. PATENT DOCUMENTS

| | | |
|---|---|---|
| 4,044,286 A | 8/1977 | Adams et al. |
| 4,506,569 A | 3/1985 | Brown et al. |
| 4,539,560 A | 9/1985 | Fleck et al. |
| 4,934,468 A | 6/1990 | Koerber, Sr. et al. |
| 5,161,274 A | 11/1992 | Hayes et al. |
| 5,247,938 A | 9/1993 | Silverstein et al. |
| 5,291,181 A | 3/1994 | DePonte |
| 5,561,412 A | 10/1996 | Novak et al. |

(Continued)

OTHER PUBLICATIONS

Collins, et al.;Temperature and biochemical studies of joint inflammation; Annals of the Rheumatic Diseases; vol. 29(4); Jul. 1970; pp. 386-392.

*Primary Examiner* — Catherine B Kuhlman (57) ABSTRACT

A method and system enabling delivery of a therapy type is provided. The method includes receiving a value of a parameter measured by physical sensors while a mammal is in contact with a first subset of the physical sensors. A second subset of the physical sensors, whose received value differs from a predetermined reference value of an environmental parameter, is determined. A physical part subset of the second subset, corresponding to a specified body part, is determined by utilizing the second subset and virtual data for identifying virtual sensors spatially distributed to map a space occupied by the mammal's body parts. In response, a therapy device positioned in sufficiently close proximity to the specified body part to effectively deliver the specified therapy type to the specified body part, is determined and a control signal is generated and transmitted to the associated therapy device.

19 Claims, 7 Drawing Sheets

(56) References Cited

U.S. PATENT DOCUMENTS

| | | |
|---|---|---|
| 5,636,394 A | 6/1997 | Bartley |
| 5,699,038 A | 12/1997 | Ulrich et al. |
| 5,715,548 A | 2/1998 | Weismiller et al. |
| 5,771,511 A | 6/1998 | Kummer et al. |
| 5,838,223 A | 11/1998 | Gallant et al. |
| 5,873,137 A * | 2/1999 | Yavets-Chen .................... 5/713 |
| 6,021,533 A | 2/2000 | Ellis et al. |
| 6,067,019 A | 5/2000 | Scott |
| 6,133,837 A | 10/2000 | Riley |
| 6,185,767 B1 | 2/2001 | Brooke et al. |
| 6,208,250 B1 | 3/2001 | Dixon et al. |
| 6,279,183 B1 | 8/2001 | Kummer et al. |
| 6,320,510 B2 | 11/2001 | Menkedick et al. |
| 6,321,878 B1 | 11/2001 | Mobley et al. |
| 6,336,235 B1 | 1/2002 | Ruehl |
| 6,362,725 B1 | 3/2002 | Ulrich et al. |
| 6,505,368 B1 | 1/2003 | Ellis et al. |
| 6,584,628 B1 | 7/2003 | Kummer et al. |
| 6,691,346 B2 | 2/2004 | Osborne et al. |
| 6,694,549 B2 | 2/2004 | Perez et al. |
| 6,708,358 B2 | 3/2004 | Hensley |
| 6,791,460 B2 | 9/2004 | Dixon et al. |
| 6,876,303 B2 | 4/2005 | Reeder et al. |
| 6,892,405 B1 | 5/2005 | Dimitriu et al. |
| 6,957,461 B2 | 10/2005 | Osborne et al. |
| 6,978,500 B2 | 12/2005 | Osborne et al. |
| 7,092,376 B2 | 8/2006 | Schuman |
| 7,171,708 B2 | 2/2007 | Osborne et al. |
| 7,237,287 B2 | 7/2007 | Weismiller et al. |
| 7,260,860 B2 | 8/2007 | Chambers et al. |
| 7,296,312 B2 | 11/2007 | Menkedick et al. |
| 7,315,535 B2 | 1/2008 | Schuman |
| 7,319,386 B2 | 1/2008 | Collins, Jr. et al. |
| 7,325,265 B2 | 2/2008 | Hornbach et al. |
| 7,330,127 B2 | 2/2008 | Price et al. |
| 7,389,552 B1 | 6/2008 | Reed et al. |
| 7,406,731 B2 | 8/2008 | Menkedick et al. |
| 7,443,302 B2 | 10/2008 | Reeder et al. |
| 7,451,506 B2 | 11/2008 | Kummer et al. |
| 7,454,805 B2 | 11/2008 | Osborne et al. |
| 7,458,119 B2 | 12/2008 | Hornbach et al. |
| 7,464,605 B2 | 12/2008 | Douglas et al. |
| 7,469,436 B2 | 12/2008 | Meyer et al. |
| 7,480,951 B2 | 1/2009 | Weismiller et al. |
| 7,487,562 B2 | 2/2009 | Frondorf et al. |
| 7,500,280 B2 | 3/2009 | Dixon et al. |
| 7,520,006 B2 | 4/2009 | Menkedick et al. |
| 7,523,515 B2 | 4/2009 | Allen et al. |
| 7,533,429 B2 | 5/2009 | Menkedick et al. |
| 7,610,637 B2 | 11/2009 | Menkedick et al. |
| 7,610,638 B2 | 11/2009 | Kramer et al. |
| 7,617,555 B2 | 11/2009 | Romano et al. |
| 7,657,956 B2 | 2/2010 | Stacy et al. |
| 7,676,862 B2 | 3/2010 | Poulos et al. |
| 7,676,872 B2 | 3/2010 | Block et al. |
| 7,690,059 B2 | 4/2010 | Lemire et al. |
| 7,715,387 B2 | 5/2010 | Schuman |
| 7,743,441 B2 | 6/2010 | Poulos et al. |
| 7,757,318 B2 | 7/2010 | Poulos et al. |
| 7,779,493 B2 | 8/2010 | Lemire et al. |
| 7,779,494 B2 | 8/2010 | Poulos et al. |
| 7,784,128 B2 | 8/2010 | Kramer |
| 8,051,513 B2 | 11/2011 | Reed et al. |
| 8,155,918 B2 | 4/2012 | Reed et al. |
| 8,156,586 B2 | 4/2012 | Reed et al. |
| 2004/0046668 A1* | 3/2004 | Smith et al. ................. 340/573.7 |
| 2004/0231052 A1 | 11/2004 | Gladney |
| 2005/0190068 A1 | 9/2005 | Gentry et al. |
| 2005/0203493 A1 | 9/2005 | Kuroda et al. |
| 2006/0034726 A1 | 2/2006 | Sunshine et al. |
| 2006/0107459 A1 | 5/2006 | Gladney |
| 2006/0168730 A1 | 8/2006 | Menkedick et al. |
| 2007/0056101 A1 | 3/2007 | Mahajan et al. |
| 2007/0130692 A1 | 6/2007 | Lemire et al. |
| 2007/0132597 A1 | 6/2007 | Rodgers |
| 2007/0136102 A1 | 6/2007 | Rodgers |
| 2007/0180616 A1 | 8/2007 | Newkirk et al. |
| 2007/0210917 A1 | 9/2007 | Collins, Jr. et al. |
| 2008/0015903 A1 | 1/2008 | Rodgers |
| 2008/0021731 A1 | 1/2008 | Rodgers |
| 2008/0120784 A1 | 5/2008 | Warner et al. |
| 2008/0122616 A1 | 5/2008 | Warner et al. |
| 2008/0126122 A1 | 5/2008 | Warner et al. |
| 2008/0126132 A1 | 5/2008 | Warner et al. |
| 2008/0147442 A1 | 6/2008 | Warner et al. |
| 2008/0201429 A1 | 8/2008 | Barbell et al. |
| 2008/0224861 A1 | 9/2008 | McNeely et al. |
| 2008/0235872 A1 | 10/2008 | Newkirk et al. |
| 2009/0091458 A1 | 4/2009 | Deutsch |
| 2009/0165207 A1 | 7/2009 | Reed et al. |
| 2009/0165208 A1 | 7/2009 | Reed et al. |
| 2009/0222988 A1 | 9/2009 | Reed et al. |
| 2009/0310741 A1 | 12/2009 | Borghese et al. |
| 2010/0088119 A1 | 4/2010 | Tipirneni |
| 2010/0318239 A1* | 12/2010 | Oexman et al. ................. 700/301 |
| 2011/0239370 A1* | 10/2011 | Turo et al. ........................ 5/600 |
| 2011/0263950 A1* | 10/2011 | Larson et al. ................. 600/301 |
| 2012/0053423 A1 | 3/2012 | Kenalty et al. |
| 2012/0053424 A1* | 3/2012 | Kenalty et al. ................. 600/300 |
| 2012/0137436 A1 | 6/2012 | Andrienko |
| 2012/0323501 A1 | 12/2012 | Sarrafzadeh et al. |
| 2013/0090571 A1 | 4/2013 | Nourani et al. |

* cited by examiner

SMART SURFACE BIOLOGICAL SENSOR AND THERAPY ADMINISTRATION

RELATED APPLICATIONS

This application claims the benefit under 35 U.S.C. 119(e) of prior U.S. Provisional Patent Application No. 61/964,372 filed Jan. 4, 2014.

FIELD

The present invention relates generally to a method for sensing biological parameters and in particular to a method and associated system for delivering specified therapy to body portions based on sensed biological parameters.

BACKGROUND

Sleep entails a long period of time of body contact with a surface. Persons deemed to benefit from various therapy types administered to specific body parts may find it time-efficient and effective to receive therapy while in contact with a surface enabled to deliver therapy to body parts such as a mattress. Accordingly, there exists a benefit to enable therapy delivery from a surface to body parts.

SUMMARY

A first aspect of the invention provides a method for enabling delivery of a specified therapy type to a specified body part of mammal, over specified periods of time, the method comprising for each specified period of time: receiving, by a processor from physical sensors of a plurality of physical sensors spatially distributed on or in a substrate, a value of an environmental parameter measured by the physical sensors while the mammal is on or in contact with a substrate and in contact with a first subset of the plurality of physical sensors, leaving a remaining subset of the plurality of physical sensors not in contact with the mammal; determining, by the processor, a second subset of the plurality of physical sensors as being those physical sensors whose received value differs from a corresponding predetermined reference value, of the environmental parameter, specific to the physical sensors; determining, by the processor, a physical part subset of the second subset, the physical part subset corresponding to the specified body part, the determining the physical part subset comprising utilizing the second subset and virtual data for identifying a plurality of virtual sensors spatially distributed to map a space occupied by the mammal's body parts; determining, by the processor from the physical part subset, an associated therapy device of a group of therapy devices spatially distributed on or in the substrate, wherein the associated therapy device is positioned in sufficiently close proximity to the specified body part to effectively deliver the specified therapy type to the specified body part; generating, by the processor, a control signal comprising instructions to deliver the specified therapy type to the specified body part; transmitting, by the processor, the control signal to the associated therapy device to activate the associated therapy device to deliver the specified therapy type to the specified body part; and after the transmitting, if the each specified period of time has elapsed then terminating the method, otherwise repeating the receiving, the determining the second subset, the determining the physical part subset, the determining the associated therapy device, the generating, and the transmitting.

A second aspect of the invention provides a computer program product, comprising a computer readable hardware storage device storing a computer readable program code, the computer readable program code comprising an algorithm that when executed by a computer processor of a computing system implements a method, the method comprising: receiving, by the processor from physical sensors of a plurality of physical sensors spatially distributed on or in a substrate, a value of an environmental parameter measured by the physical sensors while the mammal is on or in contact with a substrate and in contact with a first subset of the plurality of physical sensors, leaving a remaining subset of the plurality of physical sensors not in contact with the mammal; determining, by the processor, a second subset of the plurality of physical sensors as being those physical sensors whose received value differs from a corresponding predetermined reference value, of the environmental parameter, specific to the physical sensors; determining, by the processor, a physical part subset of the second subset, the physical part subset corresponding to the specified body part, the determining the physical part subset comprising utilizing the second subset and virtual data for identifying a plurality of virtual sensors spatially distributed to map a space occupied by the mammal's body parts; determining, by the processor from the physical part subset, an associated therapy device of a group of therapy devices spatially distributed on or in the substrate, wherein the associated therapy device is positioned in sufficiently close proximity to the specified body part to effectively deliver the specified therapy type to the specified body part; generating, by the processor, a control signal comprising instructions to deliver the specified therapy type to the specified body part; transmitting, by the processor, the control signal to the associated therapy device to activate the associated therapy device to deliver the specified therapy type to the specified body part; and after the transmitting, if the specified interval of time has elapsed then terminating the method, otherwise performing the receiving, the determining the second subset, the determining the physical part subset, the determining the associated therapy device, the generating, and the transmitting.

A third aspect of the invention provides a method for enabling delivery of a specified therapy type to a specified body part of mammal, over specified periods of time, the method comprising for each specified period of time: receiving, by a processor from a subset of physical sensors of a plurality of physical sensors spatially distributed on or in a substrate, tag data identifying a tag attached to the specified body part while the mammal is on or in contact with a substrate; analyzing, by the processor, mapping data comprising associations between the plurality of physical sensors and a group of therapy devices spatially distributed on or in the substrate; determining, by the processor based on the analyzing, an associated therapy device of a group of therapy devices corresponding to the subset of physical sensors and the specified body part, wherein the associated therapy device is positioned in sufficiently close proximity to the specified body part to effectively deliver the specified therapy type to the specified body part; generating, by the processor, a control signal comprising instructions to deliver the specified therapy type to the specified body part; transmitting, by the processor, the control signal to the associated therapy device to activate the associated therapy device to deliver the specified therapy type to the specified body part; and after the transmitting, if the each specified period of time has elapsed then terminating the method, otherwise repeating the receiving, the analyzing, the determining, the generating, and the transmitting.

The present invention advantageously provides a simple method and associated system capable of enabling therapy delivery from a surface to body parts.

DETAILED DESCRIPTION

Figure 1:
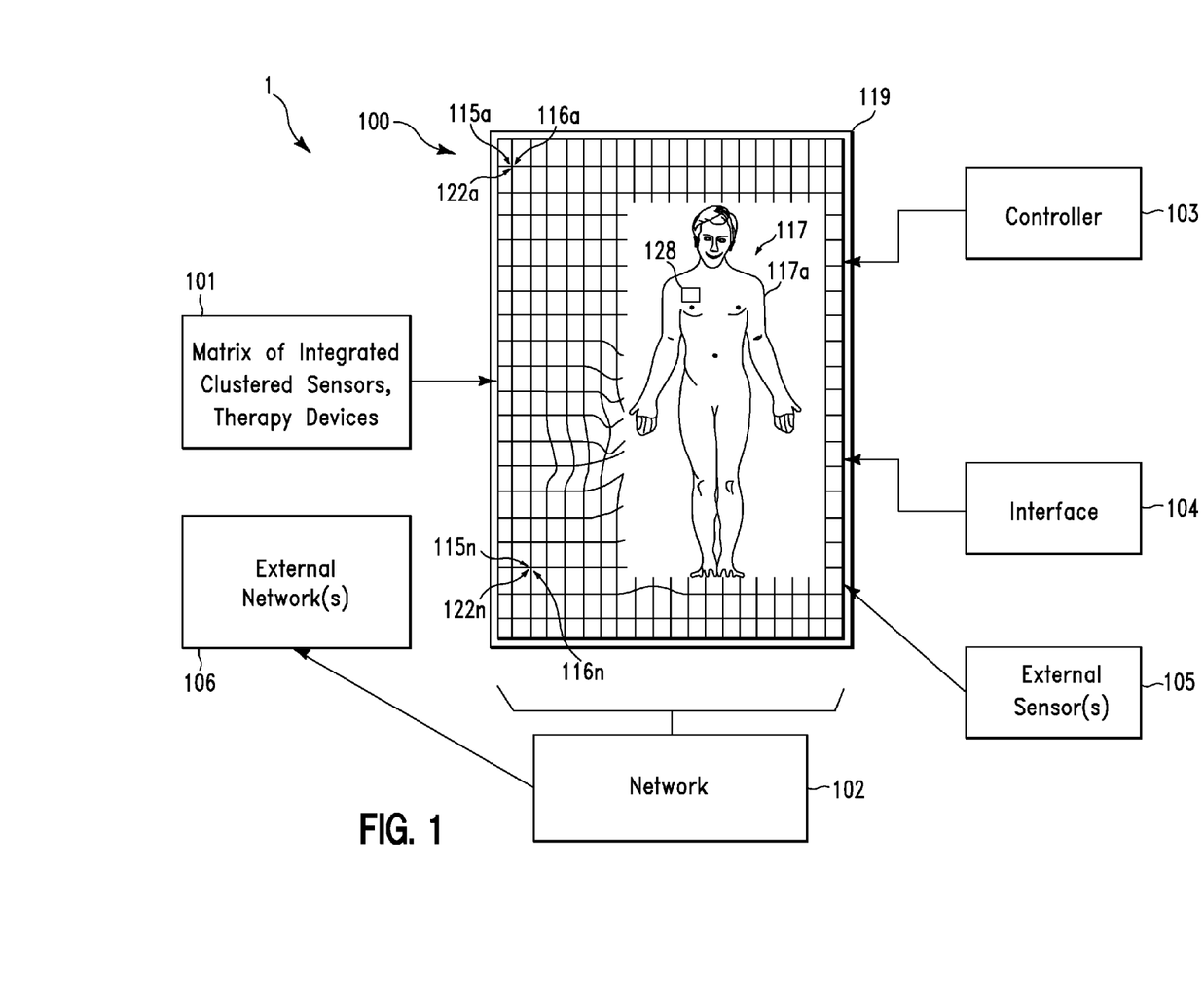
FIG. 1 illustrates a system for automatically sensing a body part and automatically delivering an associated therapy, in accordance with embodiments of the present invention.

FIG. 1 illustrates a system 1 for automatically sensing a body portion (i.e., part) and automatically delivering an associated therapy, in accordance with embodiments of the present invention. System 1 includes a smart matrix 100 (comprising a substrate 119 and a matrix 101) connected to a controller 103, an interface 104, external sensors 105, and an external network 106. Matrix 101 includes sensors 115a . . . 115n and therapy devices 116a . . . 116n located at a plurality of nodes 122a . . . 122n at each intersection point of a grid of matrix 100. The sensors 115a . . . 115n and therapy devices 116a . . . 116n may include independent sensors and independent therapy devices each located within discrete housings. Alternatively, the sensors 115a . . . 115n and therapy devices 116a . . . 116n may include housings each comprising at least one sensor and at least one therapy device located within a same housing. The sensors 115a . . . 115n and therapy devices 116a . . . 116n may be comprised by or connected to an array of receptor means (e.g., sockets) integral with a removable grid apparatus comprised by the substrate 119. System 1 may be applied to a smart garment where a portion of the garment is associated with a body part, such as a right shoulder. Accordingly, the body part identification aspects of system 1 may not be required. System 1 enables the steps of garment user identification, sensing of body contact, and administering programmed therapies.

System 1 enables a method for identifying and locating a position of a portion/body part (e.g., a portion 117a, such as an arm) of a body of a mammal 117 (e.g., a human being, a non-human mammal, etc.) and administering a determined therapy to the portion of the body of the mammal 117. A portion of a body of a mammal 117 may include any body part including, inter alia, an arm, a leg, a hand, a finger, a back, a foot, any type of muscle, etc. The portion of the body of the mammal 117 is located in sufficiently close proximity to the substrate 119. The substrate 119 may be, inter alia, a mattress, a slip cover, wearable material, a chair, a wheelchair, etc. Substrate 119 comprises networked sensors 115a . . . 115n for sensing a value(s) of biological parameters of a portion(s) of a body for identifying and determining a position of a portion(s) of the body on the substrate 119.

The substrate 119 additionally comprises integrated and networked therapy devices 116a . . . 116n capable of administering a specified therapy(s) to the portion(s) of the body on the substrate 119. The integrated and networked therapy devices 116a . . . 116n may comprise any type of therapy device and are configured to deliver any type of therapy including, inter alai, magnetic therapy, light therapy, infrared therapy, laser therapy, temperature-based therapy, shockwave therapy, ultrasound therapy, acoustic therapy, vibration therapy, massage therapy, electronic therapy, chemical therapy, electromagnetic therapy, and electromechanical therapy.

The sensors 115a . . . 115n and therapy devices 116a . . . 116n may be controlled via a programmable logic means executed by a controller 103. Matrix 101 may comprise sensors 115a . . . 115n and therapy devices 116a . . . 116n in differing sections of an array including one or more of each type of sensor and therapy device. A nature, location, degree, and/or duration of a determined therapy may be a function of, inter alia, a determined location of a portion(s) of a body on the substrate 119, a sensed biological parameter(s) of the portion(s) of a body, therapy control logic and calibration of a therapeutic delivery means, etc. The sensors 115a . . . 115n may comprise any type of sensor configured to detect any type of body characteristics such as, inter alia, a position of a portion of a body (via, e.g., pressure and/or temperature measurements), a type of a portion of a body (e.g., an arm, a leg, etc.), an orientation and/or location on a surface of substrate 119, a temperature, acceleration, moisture, resistance, a stress level, a heart rate, a respiration rate, a blood flow rate, metabolic activity, blood oxygenation, etc. System 1 may comprise or be integrated with sleep monitor devices to modulate aspects of associated therapy devices to optimize attributes of sleep such as, inter alia, REM sleep, a sleep duration, sleep spindles for a given user, etc. An optimization process may include correlating therapy types and associated measured effects with desired sleep states of one or more users (e.g., mammals).

System 1 may be configured to modify functions of an adjustable bed and/or a mattress comprising dynamic electromechanical, hydraulic, and/or additional automatic adjustment means. For example, sensors configured to detect labored breathing (of a mammal) during a sleep cycle may direct an adjustable bed to raise or lower associated portions of the bed to modify a position of a mammal.

Matrix 101 may comprise any type of clustered array of sensors 115a . . . 115n and therapy device nodes 122a . . . 122n within specified sections (e.g., nodes 122a . . . 122n) the substrate 119. Sensors 115a . . . 115n and therapy devices 116a . . . 116n may be configured in various combinations with respect to respective features and capabilities in each grid type section of a matrix. Additionally, an external sensor(s) 105 (i.e., not integrated with substrate 119) may be connected to a network 102 for controlling matrix 101 and provide data to the network. For example, a blood pressure sensor or audio sensor (e.g., to detect snoring) for obtaining readings independent from the sensors of matrix 101.

System 1 may additionally comprise or access a database of sensor readings (i.e., virtual readings) associated with known maladies such as, inter alia, muscle spasms, shortness of breath, low blood sugar, excessive snoring, inflammation, heart attack, etc. In response, controller 103 is configured to direct a specified therapy (via a therapy device) and to wake user and/or initiate a call for assistance.

Substrate 119 includes matrix 101 comprising integrated or overlaid sensors 115a . . . 115n (for sensing environmental parameters) and therapy devices 116a . . . 116n (for delivery of specified therapies in response to the sensed biological parameters). Matrix 101 is connected (physically or wirelessly) through a dedicated (LAN, WAN, etc.) or Internet network 102 to a controller 103 (i.e., programmable logic and control unit), an (control and input/readout) interface (104), and internal local or external networks 106. The controller 103 may comprise a local and/or remote wireless controller. External networks 106 may include, inter alia, a hospital network, the Internet, etc. Substrate 119 comprises sensors 115a . . . 115n and therapy devices 116a . . . 116n (of matrix 101) in specified clusters strategically deployed to sense and interact with one or more portions of a body of one or more mammals on a surface of the substrate 119. The sensors 115a . . . 115n and therapy devices 115a . . . 115n are strategically placed across the matrix 101 are configured to sense and provide therapy to portions of a body as they change position/location over time across the matrix 101. An external sensor(s) 105 may be enabled to perform functions similar the sensors of matrix 101 (e.g., identifying a location of a portion of a body on the substrate 119).

Substrate 119 may comprise integrated and/or an external (e.g., a slip cover) matrix (e.g., matrix 101) of sensors 115a . . . 115n and therapy (delivery) devices 116a . . . 116n. For example, the substrate 119 may comprise a mattress including clusters of integrated sensors 115a . . . 115n and therapy devices 116a . . . 116n distributed throughout a surface of the mattress (e.g., comprising sockets for removably connecting to and retaining sensors 115a . . . 115n and therapy devices 116a . . . 116n). The integrated sensors 115a . . . 115n and therapy devices 116a . . . 116n are configured to be in physical or electrical contact portions of a body as they move across the surface of the mattress. The sensors 115a . . . 115n and therapy devices 116a . . . 116n may be integrated into the surface (of the substrate 119) such that they are positioned in sufficiently close proximity to the portion of the body to effectively detect desired biological parameters (e.g., temperature, respiration, pulse, pressure, etc.) and to effectively deliver desired therapies (e.g., ultrasound, infrared, electromagnetic therapy, etc.) to specific targeted portions of a body in contact with the surface of the substrate 119.

The sensors 115a . . . 115n may be integrated in clusters enabled to detect values of environmental or biological parameters from a proximal portion of a body and determine a position or orientation of the proximal portion. Environmental or biological parameters may include, inter alia, a respiration rate, a temperature, a pulse rate, moisture or sweat parameters, acceleration, resistance, stress, pressure readings, blood oxygenation, odor, brain waves, metabolic activity, blood chemicals, etc. Therapy devices 116a . . . 116n are configured to deliver a specified therapy(s) to the proximal portion of a body. The therapy devices 116a . . . 116n may be configured to deliver the specified therapy to a same portion of the body from which the sensors have detected environmental or biological parameters. Alternatively, the therapy devices 116a . . . 116n may be configured to deliver the specified therapy to a different portion of the body from which the sensors have detected the biological parameters.

Network 102 is configured to connect matrix 101, interface 104, and controller 103. The network 102 may be connected to external networks 106 via direct physical or wireless connections. Network 102 may receive inputs from sensors (of matrix 101) and transmit the inputs to controller 103. The controller 103 controls and manages the sensors, therapy devices, and network activity of the network 102. The controller 103 may be configured to manage all aspects of the network 102 and types of therapy administered to a portion of a body including, inter alia, a duration, an intensity, and a frequency of differing therapy types.

Additionally, system 1 may comprise sensors that are not physically connected to the matrix 101. For example, proximal heat sensors, motion sensors, tag sensors e.g., (RFID) or a digital camera may determine (from a distance) differing positions of a body part and communicate the differing positions with the sensing devices and therapy devices of matrix 101.

A tag sensor 128 (e.g., a smart tag) may be applied to a body part designated for a specified therapy type. The tag 128 may comprise a shape of a band aid. Sensors 115a . . . 115n are enabled to recognize a proximity of the tag 128 and system 1 associates the tag 128 location proximal to the substrate 119 with both a body part and therapy type. The aforementioned association may be encoded in the tag 128 and/or reside in a system network program or memory. A plurality of tags may be used with respect to a mammal's body. Each tag may be associated with a designated body part. A fail-safe program may additionally verify that a body part associated with a tag matches the identified body part through a sensor-processor method of identifying a body part. The controller 103 may then trigger a desired therapy to be delivered by therapy devices 116a . . . 116n proximal to the tag 128 location on the substrate 119. A sensed tag location may be dynamic over time with updated sensor proximity readings thereby enabling tracking of body part motion and activation of different, newly proximal therapy devices as the tag 128 location moves with the body part across the substrate.

Example interactions between sensors 115a . . . 115n, therapy devices 116a . . . 116n, and controller 103 may include the use of distributed pressure or thermal sensors providing pressure and/or thermal data readings to the controller 103 executing a program for identifying the mammal 117 and associated portions of a body (of the mammal 117) in contact with specified locations on the substrate 119. The identification process (for identifying the associated portions of the body of the mammal 117) may include the use of a pattern-matching program retrieving expected (e.g., previously retrieved and specific to a user) pressure or thermal patterns (e.g., virtual data digitally stored and described in association with specific portions a body such as, inter alia, a torso, attachment points to the torso associated with exterior body parts such as a head, an arm, or a leg, portions of exterior body parts such as, inter alia, an elbow, a shoulder, a gluteus, a thigh, a foot, etc. in various positions such as, inter alia, face down, back down, etc.) from a memory system. Current pressure or thermal reading patterns (retrieved by the sensors 115a . . . 115n) are matched (by the pattern-matching program) to the expected pressure or thermal patterns to determine a statistical fit in order to identify an associated portion of the body. Likewise, a relative location of the current pressure or thermal reading patterns on the substrate 119 may be used to identify the associated portion of the body. Periodic thermal or pressure readings and pattern-matching (i.e., to virtual data) may be used to track position changes of portion of the body over time. A user association may be executed by user input that affirms that for example, John Doe is located on a right side of a surface of the substrate 119. Alternatively, a biometric means for identifying John Doe may be executed as follows:

A movement history may be generated for use by a user or health practitioner. A portion of the body is associated with an area of a surface and referenced to a desired therapy (for a specified portion of body) and/or sensor recording program. If a specified therapy is designated for a specified portion of a body (e.g., infra-red for the right shoulder of John Doe), the controller 103 continuously monitors a location of John Doe's right shoulder on the surface of the substrate 119 and automatically directs the infra-red therapy device activity for cumulative desired dose duration and intensity modulation. The infrared therapy device may comprise a flexible micro LED array or fiber optic elements engineered to deliver desired wavelengths and intensity of phototherapy per unit of time. When a desired dose (of therapy) has been delivered to the right shoulder, the controller 103 disables the therapy device. During the therapy delivery, the controller 103 may use a thermal sensor to monitor a temperature of the right shoulder and modulate therapy to not exceed an upper parameter. Therefore, location detection sensors, the controller 103, therapy devices, and biological parameters are coordinated by the controller 103 to locate portions of a body specified to receive therapy, deliver the specified therapy (during position changes), and leverage additional sensors to monitor biological parameters of portions of the body and compare the biological parameters to programmed guidelines.

Sensors enabling body portion location and identification may be used with all therapy devices to enable body portion targeted therapy. Sensors for sensing environmental or biological parameters (such as temperature, moisture, respiration, and pulse) may be used in combination with therapy devices for which biological parameter data are relevant. For example, a thermal pattern of a hip may illustrate evidence of inflammation for which infrared or ultrasound therapy may be indicated. A computer program searching for specified biological readings associated with body portions may provide data to the controller 103. In response, the controller instructs one or more therapy devices (associated with specified sensors described any means such as, inter alia, a table of specified sensors associated with specified therapy devices) to deliver a desired therapy triggered by the specified biological parameter readings associated with a body portion according to prescribed doses.

Figure 2:
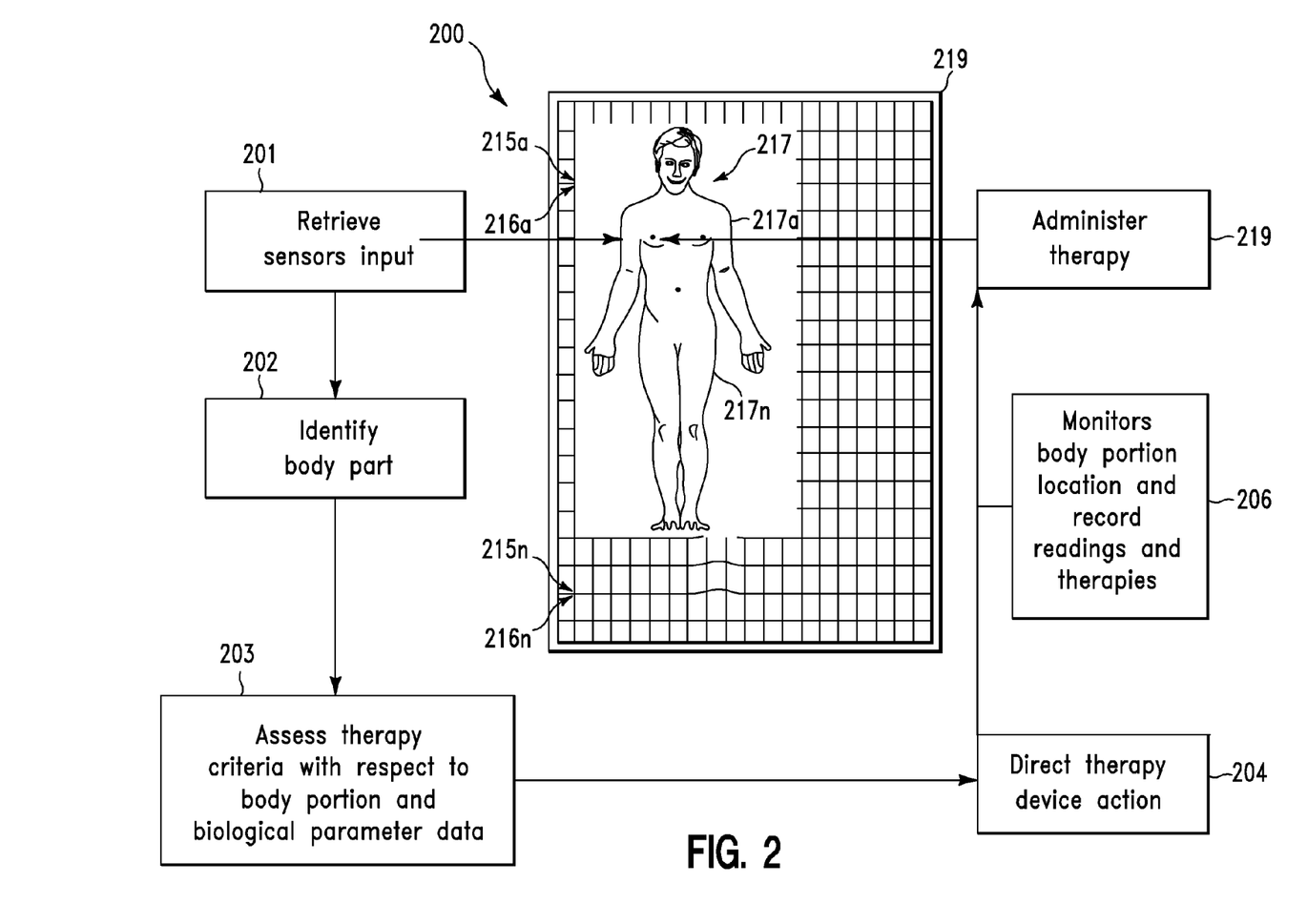
FIG. 2 illustrates an algorithm detailing a process flow enabled by the system of FIG. 1 for executing a sensing and therapy administration process, in accordance with embodiments of the present invention.

FIG. 2 illustrates an algorithm detailing a process flow enabled by system 1 of FIG. 1 for executing a sensing and therapy administration process, in accordance with embodiments of the present invention. In step 201, sensors 215a . . . 215n integrated into a smart matrix 200 (comprising a substrate 219 and a matrix 201 as described with respect to FIG. 1) retrieves values associated with biological or environmental body portion parameters (e.g., pressure or thermal patterns). In step 202, body portions are identified. Alternatively, the body portions may be inputted via input data from, e.g., a doctor. In step 203, the biological or environmental body portion parameter data identifying the body portions are transmitted to a controller. The controller identifies a location of a specified body portion (e.g., a right elbow) on a surface of the substrate 219 based on comparing biological/environmental body portion parameters to virtual data identifying virtual sensors spatially distributed to map a space occupied by the mammal's 217 body parts 217a . . . 217n as described in detail with respect to FIGS. 5 and 6, infra. In response, the controller directs (in step 204) a therapy device (of therapy devices 216a . . . 216n) to deliver (in step 205) a specified therapy to a specified body portion. For example, a right elbow of a user may be programmed to receive infrared therapy for two five minute intervals during a 6-8 hour expected sleep cycle. The controller may instruct infrared therapy devices (i.e., proximal to a current position of the right elbow) to deliver the infrared therapy at a specified intensity level for a programmed duration. Likewise, heat sensors may monitor (in step 206) a temperature of the body portions in close proximity to the active therapy devices to assure a threshold temperature is not exceeded. As the elbow may move across the substrate 219, the plurality of sensor and therapy device clusters provide readings enabling the controller to track a changing location of the right elbow and instruct and manage therapy devices to complete the desired duration of the infrared therapy.

Additionally, sensor activation may be triggered by pressure or thermal sensed changes with respect to a threshold magnitude. Therapy devices may be located proximal to sensors and the sensors and therapy devices may be sized and situated to fit a displacement of a body portion. For example, an adult shoulder may require 4 inch by 4 inch clusters of sensors and therapy devices.

Tracking and identifying an orientation and location of body portions on substrate 219 may enable providing specified on-going therapy to a specified body portion as it shifts orientation and location on the substrate 219. The tracking and identification process may be enabled by monitoring sensor readings of sensors 215a . . . 215n of the smart matrix 200. Alternatively, the tracking and identification process may be enabled by monitoring a position of body portions on the substrate 219 through the use of digital imaging (e.g., by a remote camera) that compares imaged body portion positions on a digitized representation of the substrate 219 to rules or stored virtual parameters regarding determining a body portion position on the substrate 219. Additionally, sensor readings of pressure or temperature distribution on portions of the substrate 219 may likewise be compared to virtual parameters (e.g., stored baseline data) for evaluating a distribution in determining which body portion is responsible for generating a sensed distribution. Therefore, sensors 215a . . . 215n of matrix 201 may provide inputs enabling a logic program to determine a body portion type, an associated location, and change in location. For example, a specified section of a grid may be associated with a head of a body or a left arm. A pattern of expected or typical pressure or temperature patterns (virtual baseline data associated with a specified user) may be associated with a body portion and an associated location and detected changes in the aforementioned patterns may be associated with a position shift of body portions on a surface of the substrate 219. Accordingly, a program managing the matrix 201 of sensors 215a . . . 215n and therapy devices 216a . . . 216n may determine, track, and change a location of active therapy devices and/or therapy features as body portions are determined to have shifted orientation or position/location on the surface the substrate 219 thereby shifting the activation of differing sensors and/or therapy devices.

Furthermore, a body portion location, type, and change in orientation may be determined by an overhead optical or heat sensors comprised by the matrix 201. The overhead optical or heat sensors may be programmed to detect changes in patterns of pressure or heat on various segments of the substrate 219. For example, an overhead optical system may compare a time series of images of a body on a surface with respect to a representation of the substrate 219 and associated locations (e.g., a grid) to determine changes and changes in location with respect to a grid comprising various body portions.

Alternatively, an identity of a mammal's location on the substrate 219 may be referenced by a manual or biometric entry into a computer program control module networked with an active therapy surface such that a surface location may be associated with the identity of the mammal and desired therapy types for targeted body portions. For example, a user (i.e., a mammal) may enter a side of a bed or provide a biometric reading on a control module (via an interface) confirming a side of a bed that they will use.

The following implementation example describes a process for initiating a specified therapy type triggered by sensor readings to a controller thereby triggering a desired therapy process pre-programmed by a user (e.g., a clinician). In this implementation, a condition of (for example) rheumatoid arthritis of a right shoulder may require infrared therapy. In response, a specified infrared therapy is programmed to trigger upon sensor readings for a body portion temperature exceeding predetermined parameters. The process is initiated when a body portion is identified (i.e., the right shoulder) and tracked for location on the substrate 219. Additionally, biological parameter sensed readings (e.g., temperature) with respect to the body portion are retrieved. If the temperature of the targeted body portion exceeds a predetermined parameter, the specified therapy (e.g., infrared) is triggered by the controller.

Additionally, the controller monitors a location (of the targeted body portion) and a total therapy duration and intensity during delivery of the therapy. The aforementioned process determines movement of the body portion over time and a time during which the body portion may be unavailable for therapy due to lack of adequate contact with substrate areas and associated therapy devices. When a desired duration and intensity of therapy is delivered, the controller disables therapy. Sensor readings and therapy administration details may disable the associated therapy device.

Figure 3:
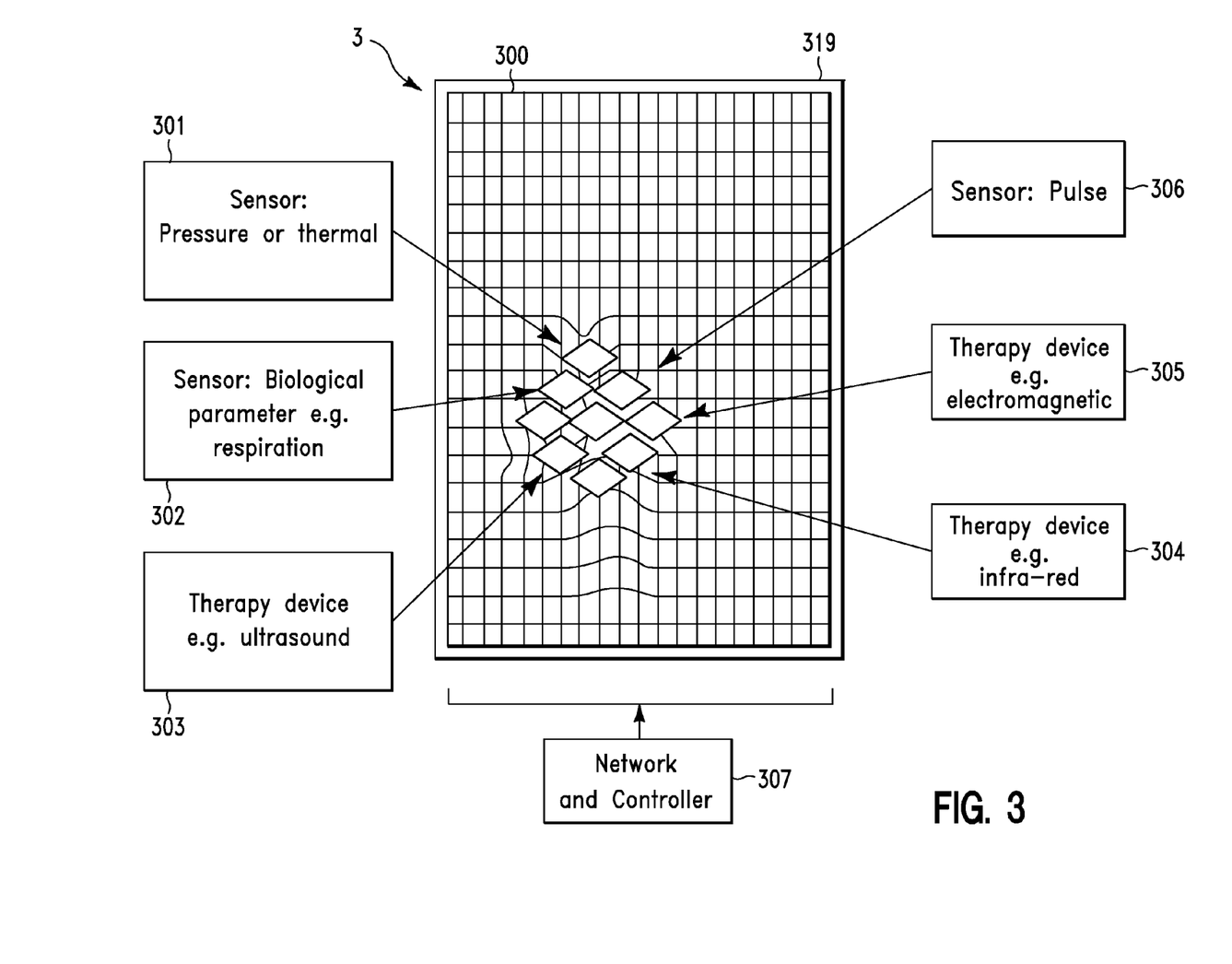
FIG. 3 illustrates a sensor and therapy device cluster configuration, in accordance with embodiments of the present invention.

FIG. 3 illustrates a sensor and therapy device cluster configuration 3, in accordance with embodiments of the present invention. Cluster configuration 3 comprises a plurality of sensors 301, 302, and 306 and therapy devices 303, 304, and 305 (on or within a substrate 319) in close proximity to each other such that they effectively sense environmental or biological parameters of body portions and administer specified therapies to body portions. Therefore, if a target body portion comprises a portion of a shoulder, hip, or elbow, a size of individual sensors and therapy devices as well as a size of the cluster of the therapy devices is determined such that both effective sensing and therapy administration are accomplished with respect to a surface area of the body portion target. Additionally, an area comprising the plurality of sensors and therapy devices 301-306 may be equal to or less than a surface area in contact with an average adult shoulder or elbow.

The cluster configuration 3 and associated surface may be controlled by a controller and a network 307. The controller may be programmable by a user, a health care provider, etc. Programming may be enabled via a manual interface to the controller or via a network (e.g., wireless, Internet, local wired network, etc.). A program for a specific therapy type and desired clinical result with respect to a specified body portion may be programmed via therapy devices 303, 304, and 305 and monitored by sensors 301, 302, and 306 through a local or remote monitor or device such as, inter alia, a mobile phone. Clinical results with respect to the therapy may be recorded and analyzed for optimization based on results reported by a user and/or recorded by sensors 301, 302, and 306. Records of sensor data, therapy administration aspects, and biological parameter readings of body portions may be maintained and analyzed for desired changes of an adaptive nature to therapy administration to achieve deemed improvements in effects of therapy on body portions.

Programming the controller with respect to the cluster configuration 3 may comprise user specific program code for one or more body portions. The program code may associate differing therapy types with one or more body portions. Furthermore, the program code may associate one or more biological parameters of one or more body parts with an initiation of a specified therapy and associated attributes. For example, a therapy initiation may be contingent upon a temperature, pulse, moisture, electrical resistance, and/or other biological aspects of a body portions. Therapy types may be programmed for one or more aspects comprising: duration, intensity, frequency, and association with one or more other therapy types associated with one or more body portions.

Therapy effectiveness may be determined by sensor readings from sensors 301, 302, and 306 proximal to a target body portion retrieved before, during, and/or after a therapy. Therapy may be programmed to be actively adaptive to changes in one or more biological parameter readings of a body portion by sensors. For example, infra-red therapy may be modulated as a function of changing temperature of a body portion. Therapy may be actively managed by a controller for one or more users of an active therapy surface simultaneously. Multiple therapy types may be programmed for interaction and timing.

Figure 4:
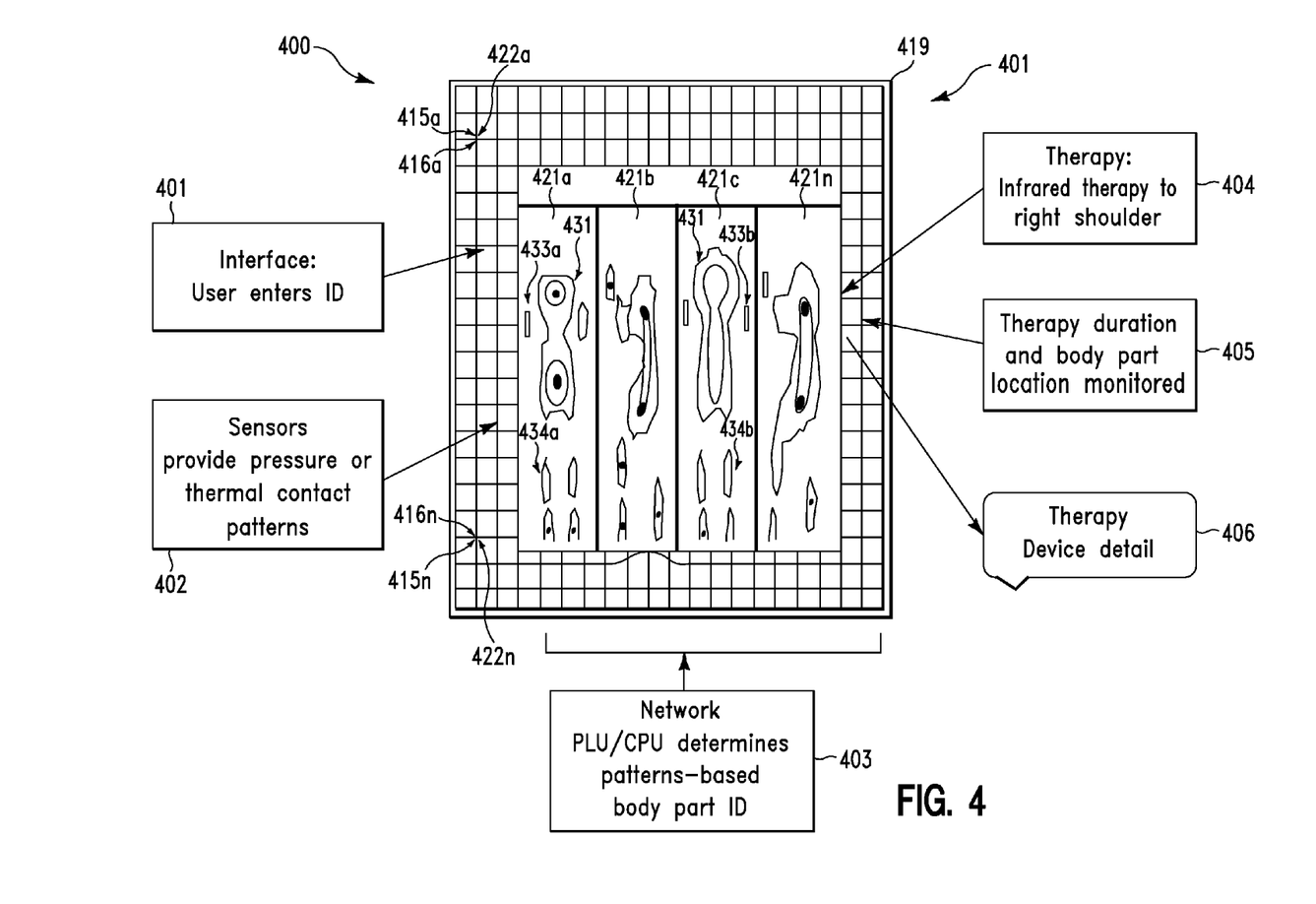
FIG. 4 illustrates an algorithm detailing a process flow enabled by the system of FIG. 1 for executing a body part location determination and therapy management process, in accordance with embodiments of the present invention.

FIG. 4 illustrates an algorithm detailing a process flow enabled by system 1 of FIG. 1 for executing a body part location determination and therapy management process, in accordance with embodiments of the present invention. FIG. 4 illustrates a matrix 400 (comprising a substrate 419 and a matrix 401). Matrix 401 includes sensors 415a . . . 415n and therapy devices 416a . . . 416n located at a plurality of nodes 422a . . . 422n at each intersection point of a grid of matrix 400.

FIG. 4 illustrates body part and relationship patterns 421a . . . 421n of body parts with respect to each other. For example, a face-down position pattern or orientation (as illustrated by pattern 421c) may be indicated by a relative pressure or temperature spike (i.e., as illustrated by the various shading conditions) caused by lack of elbow imprints 433b but presence of knee imprints 434b in areas to the side and below that of the largest or torso area 431. Likewise, a face-up position or orientation 421a would present sharper elbow imprints 433a but less pronounced relative pressure or thermal imprints 434a where knees are expected relative to the torso 431 and its orientation given the relative head pattern with respect to the torso pattern. Similarly, the a left side pattern or orientation 421b or right side pattern or orientation 421n is easily distinguished by the orientation of pressure patterns around the torso of arms and legs and how they are angled. The algorithm comprises a function of general geometric pattern types or reference patterns associated with body parts in different body positions and the relative arrangement of these patterns associated with each position. A mathematical depiction of a body pattern may be matched to a best fit of an observed pattern and further matched to expected relative spatial patterns of body parts to determine orientation of the body and the specific body part. Various means of best-fit determination may be used. For example, a relative proportion of body parts with respect to each other associated with various axis drawn through each pattern (i.e., patterns 421a . . . 421n) may be matched to a reference set of proportions for a body part pattern in a given body orientation. A further step of assessing a relative special distribution of body parts in each body orientation may be taken to increase a level of certainty. An additional method may measure a relative proportion of an area subtracted from a grid virtually drawn around a body part pattern and via measuring relative proportions of a negative area instead of a positive area.

In step 401, a user enters an ID (identifying the user) and associated data into an interface (e.g., interface 104 of system 1 of FIG. 1). For example, the associated data may specify a side of a bed typically used by the user. The system (e.g., system 1) may be programmed with desired therapy types of the user and necessary sensed body parameter data types.

In step 402, readings from pressure or thermal sensors are retrieved from the matrix 401 and compared to programmed baseline body part distribution patterns in step 403. The baseline body part distribution patterns may include, inter alia, specific digital patterns or maps comprising expected dimensions for a head, shoulder, torso, hip, thigh, calf, ankle or foot, hand, elbow in expected relative locations on the substrate 419 or matrix 401. In response, software (executed by a controller) computes a best fit of an observed pattern with respect to stored patterns to determine target body parts on the matrix 401 or substrate 419 in steps 404, 405, and 406. For example, if a right shoulder is programmed to receive 10 minutes of infrared therapy at a desired therapy intensity and the right shoulder location is determined, a controller directs infrared therapy device(s) (i.e., determined to be under or near the right shoulder) to administer the desired therapy 420 (i.e., an LED light array on the substrate 419). Additionally or alternatively, a location of a body portion may be determined by an overhead digital image of the body on the substrate 419 as compared to a stored digital map of the substrate 419. Furthermore, the controller may activate sensor readings to determine a temperature of the body portion receiving infrared therapy to assure that it remains within predetermined thresholds. Sensor readings may indicate a change in location of the right shoulder as a user moves. In response, the controller re-computes a new location of the target body portion, deactivates therapy devices that are no longer proximal to the target body portion, and activates proximal therapy devices while monitoring a total desired delivery of the therapy.

Figure 5:
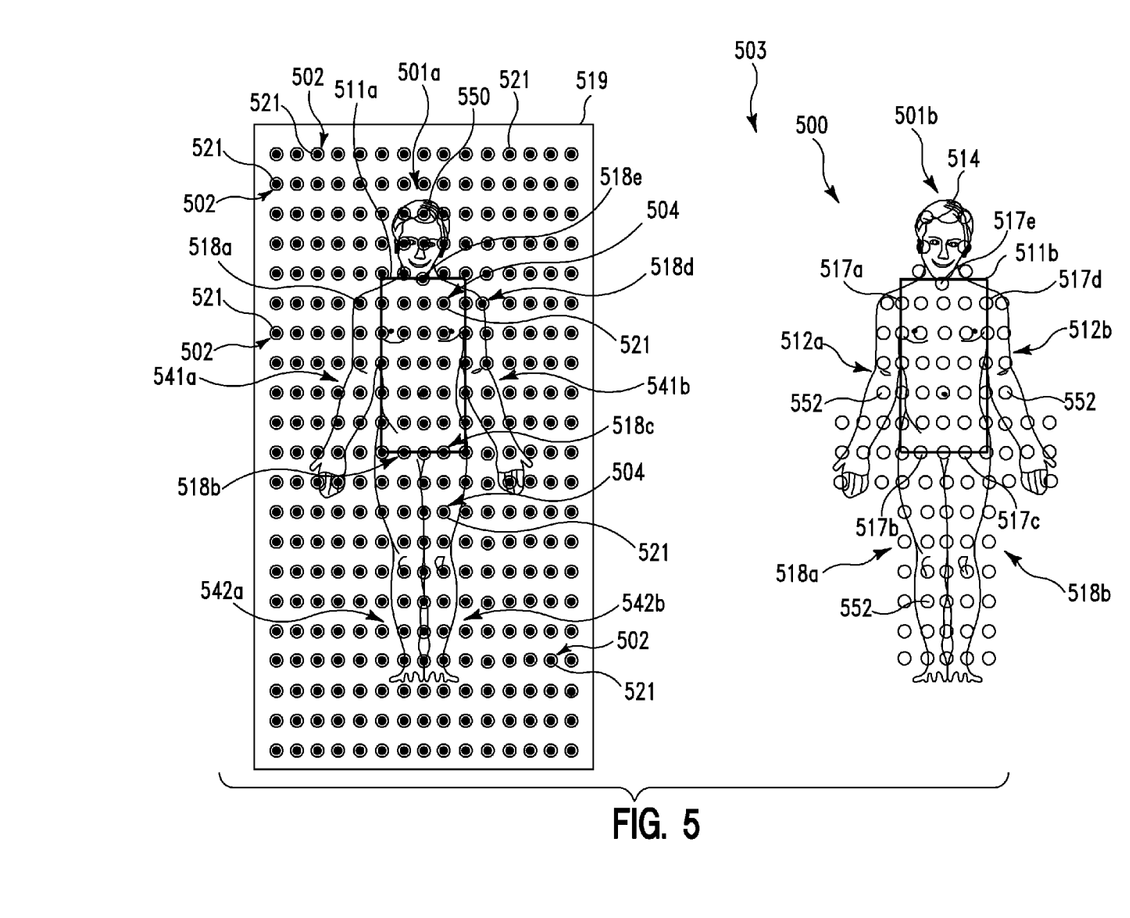
FIG. 5 illustrates a system for implementing a torso based method for determining therapy devices associated with a body part specified for therapy, in accordance with embodiments of the present invention.

FIG. 5 illustrates a system 503 for implementing a torso based method for determining therapy devices associated with a body part specified for therapy, in accordance with embodiments of the present invention. The specified body part may be specified as input data from a doctor or determined by sensor readings. System 503 illustrates a mammal 501a residing on a substrate 519 comprising (physical) sensors 502 and 504 and associated therapy devices 521. The sensors 502 represent sensors that have not been activated or comprise a specified reference value indicating that the no portions of the mammal 501a are located on or over the sensors 502. Sensors 502 may comprise an integrated sensor/therapy device (i.e., with one of therapy devices 521) apparatus. Alternatively, sensors 502 may comprise an independent sensor and an independent therapy device (i.e., one of therapy devices 521). The sensors 504 represent sensors that have been activated or comprise a received value differing from the specified reference value (e.g., by a predetermined threshold) indicating that portions mammal 501a are located on or over the sensors 504. Sensors 504 may comprise an integrated sensor/therapy device (i.e., with one of therapy devices 521) apparatus. Alternatively, sensors 504 may comprise an independent sensor and an independent therapy device (i.e., one of therapy devices 521). Additionally, sensors 518a . . . 518e represent overlapping sensors describing attachment points between a torso 511a of the mammal 501a and exterior body parts 541a, 541b, 542a, 542b, and 550 (or limbs) of the mammal (e.g., arms legs, head, etc.). System 503 additionally illustrates a set of virtual data 500 representing virtual sensors 552 (identifying a virtual representation 501b of a body of the mammal 501a) and (attachment point) virtual sensors 517a . . . 517e spatially distributed to map to a space (i.e., on the substrate 519) occupied by the mammal 501a. The virtual sensors 552 and virtual sensors 517a . . . 517e are not physical sensors but are data representations of physical sensors. The virtual sensors 552 are identified in groups representing specified body parts. For example, all virtual sensors 552 in group 511a represent a torso of the virtual representation 501b. As an additional example, virtual sensors 552 in groups 512a, 512b, 518a, 518b, and 514 represent exterior body parts (i.e., arms, legs, and a head) of the virtual representation 501b. The virtual sensors 517a . . . 517e comprise attachment point sensors representing common attachment points between group 511a of virtual sensors 552 (representing a virtual torso) and groups 512a, 512b, 518a, 518b, and 514 of virtual sensors 552 (representing virtual exterior body parts). The torso based method (enabled by system 503) for determining therapy devices associated with the body part specified for therapy includes mapping (e.g., by overlaying) the group 511b of virtual sensors 552 (i.e., representing a virtual torso) to a subset (i.e., associated with a torso 511a of the mammal 501a) of the (e.g., activated) sensors 504 to determine a match. The match determines a location of the torso 511a (on the substrate 519) of the mammal 501a. Additionally, a virtual part subset (of the virtual sensors 552) corresponding to the body part specified for therapy is determined.

The virtual part subset of the group 511b of virtual sensors 552 in combination with the group 511b of virtual sensors 552 is used to determine a subset of sensors 504 corresponding to the body part specified for therapy. If the body part specified for therapy is determined to reside within the torso 511a of the mammal 501a then the virtual part subset is mapped (e.g., by overlaying) to the group 511b of virtual sensors 552 to determine the subset of sensors 504 corresponding to the body part specified for therapy. If the body part specified for therapy is determined to comprise an exterior (to the torso 511a) body part (e.g., arm, leg, head, etc.) then a group of exterior virtual sensors (i.e., one of groups 512a, 512b, 518a, 518b, and 514) corresponding to an exterior body part (i.e., the body part specified for therapy) of the mammal 501a attached (to the mammal 501a) at a point of attachment on the torso 511a. The group of exterior virtual sensors includes the virtual part subset and includes an attachment sensor (one of virtual sensors 517a . . . 517e) coinciding with an attachment sensor (one of virtual sensors 517a . . . 517e) of the torso virtual sensors corresponding to the point of attachment. The attachment sensor of the exterior virtual sensors may comprise a same or differing sensor from the attachment sensor of the torso virtual sensors. A corresponding (i.e., to the attachment sensor of the torso virtual sensors) attachment sensor 518a . . . 518e of the torso subset (i.e., associated with a torso 511a of the mammal 501) of the sensors 504 is selected (e.g., from a table of associated virtual and physical attachment sensors). An exterior subset of the sensors 504 associated with an exterior body part (e.g., arm, leg, head, etc.) is determined by mapping one of groups 512a, 512b, 518a, 518b, and 514 (i.e., a virtual part subset) to the sensors 504 in a manner that constrains the attachment sensor of the set of exterior virtual sensors to coincide with the attachment sensor of the torso subset of the sensors 504. The virtual part subset is mapped to the exterior subset of the sensors 504 to determine a physical part subset of the sensors 504. In response, a therapy device (of therapy devices 521) associated with the physical part subset is determined. The therapy device may be determined by cross referencing (e.g., using a cross reference table, an algorithm, etc.) the therapy device with the exterior subset of the sensors 504. Additionally, a control signal is generated. The control signal includes instructions to deliver specified therapy type to the specified body part. The control signal is transmitted to the associated therapy device to activate the associated therapy device to deliver the specified therapy type to the specified body part.

Figure 6:
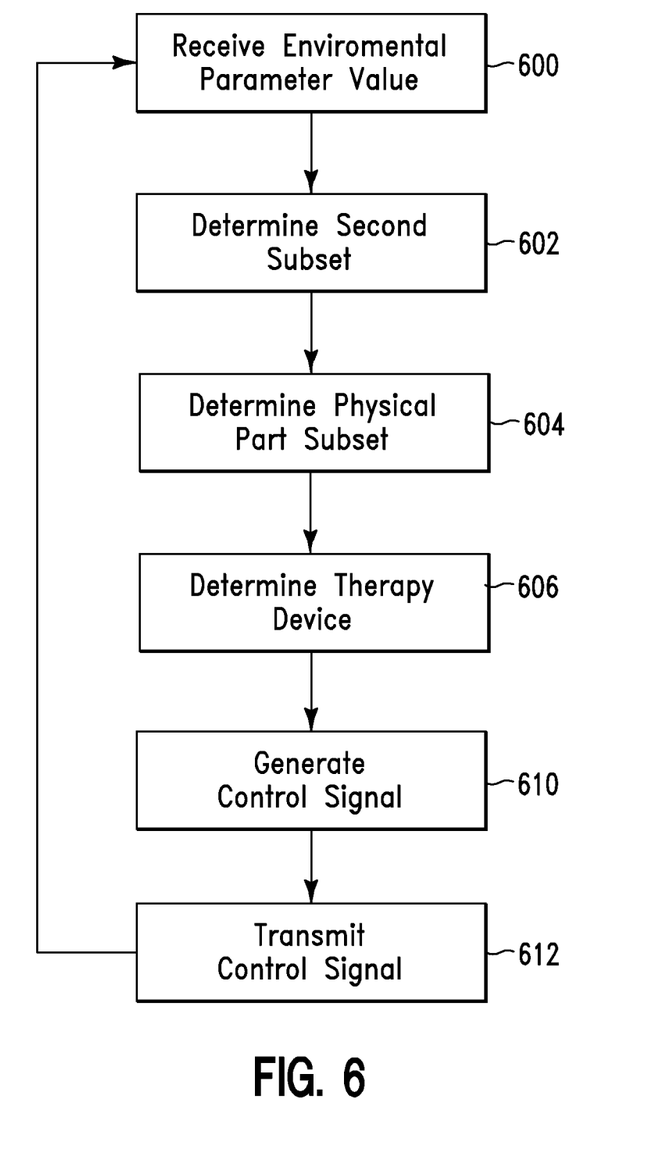
FIG. 6 illustrates an algorithm detailing a process flow enabled by the system of FIG. 1 for automatically sensing a body portion and automatically delivering an associated therapy, in accordance with embodiments of the present invention.

FIG. 6 illustrates an algorithm detailing a process flow enabled by system 1 of FIG. 1 for automatically sensing a specified body part and automatically delivering an associated therapy, in accordance with embodiments of the present invention. Each of the steps in the algorithm of FIG. 6 may be enabled and executed in any order by a computer processor executing computer code. In step 500, a value of an environmental parameter is received from physical sensors of a plurality of physical sensors spatially distributed on or in a substrate. The value of the environmental parameter is measured by the physical sensors while a mammal (e.g., a person) is on or in contact with the substrate and in contact with a first subset of the physical sensors, leaving a remaining subset of the physical sensors not in contact with the mammal. In step 602, a second subset of the physical sensors is determined as being those physical sensors whose received value differs (e.g., by a predetermined threshold value) from a corresponding predetermined reference value, of an environmental parameter, specific to the physical sensors. In step 604, a physical part subset of the second subset is determined. The physical part subset corresponds to the specified body part. Determining the physical part subset includes utilizing the second subset and virtual data for identifying a plurality of virtual sensors spatially distributed to map a space occupied by the mammal's body parts. The plurality of virtual sensors may include torso virtual sensors corresponding to a torso of the mammal and determining the physical part subset may include the following process:

1. Mapping the torso virtual sensors to the second subset of physical sensors.
2. Determining (based on the mapping) a torso subset of the second subset of physical sensors corresponding to the torso of the mammal.
3. Determining a virtual part subset of the plurality of virtual sensors corresponding to the specified body part.
4. Using the torso subset of the physical sensors and the virtual part subset to determine the physical part subset.

The specified body part may be determined to be within the torso of the mammal or external to the torso of the mammal. If the specified body part is determined to be within the torso of the mammal then using the torso subset of the physical sensors and the virtual part subset to determine the physical part subset may include mapping the virtual part subset to the torso subset to determine the physical part subset.

If the specified body part is determined to be external to the torso of the mammal then using the torso subset of the physical sensors and the virtual part subset to determine the physical part subset may include 1. Determining a set of exterior virtual sensors of the plurality of virtual sensors corresponding to an exterior body part of the mammal attached to the mammal at a point of attachment on the torso. The set of exterior virtual sensors includes the virtual part subset and comprises an attachment sensor coinciding with an attachment sensor of the torso virtual sensors corresponding to the point of attachment.
2. Determining an attachment sensor of the torso subset of the physical sensors corresponding to the attachment sensor of the torso virtual sensors.
3. Determining an exterior subset of the physical sensors by mapping the set of exterior virtual sensors to the second subset in a manner that constrains the attachment sensor of the set of exterior virtual sensors to coincide with the attachment sensor of the torso subset of the physical sensors.
4. Mapping the virtual part subset to the exterior subset of the physical sensors to determine the physical part subset.

In step 606, an associated therapy device of a group of therapy devices spatially distributed on or in the substrate is selected. The associated therapy device may be selected by selecting from an association table comprising associations between specified therapy devices and associated sensors of the physical part subset. The associated therapy device is positioned in sufficiently close proximity to the specified body part to effectively deliver the specified therapy type to the specified body part. In step 610, a control signal comprising instructions to deliver the specified therapy type to the specified body part is generated. The instructions may be received from a source external to the system 1 (e.g., from a medical professional, etc). Alternatively, the instructions may be automatically generated based on values of the environmental parameters. The instructions may include a command such as, inter alia, a duration for delivering the first specified therapy, a frequency for delivering the first specified therapy, an intensity for delivering the first specified therapy, etc. In step 612, the control signal is transmitted to the associated therapy device to activate the associated therapy device to deliver the specified therapy type to the specified body part and the process is continuously repeated to account for moving body parts and changes in therapy.

Figure 7:
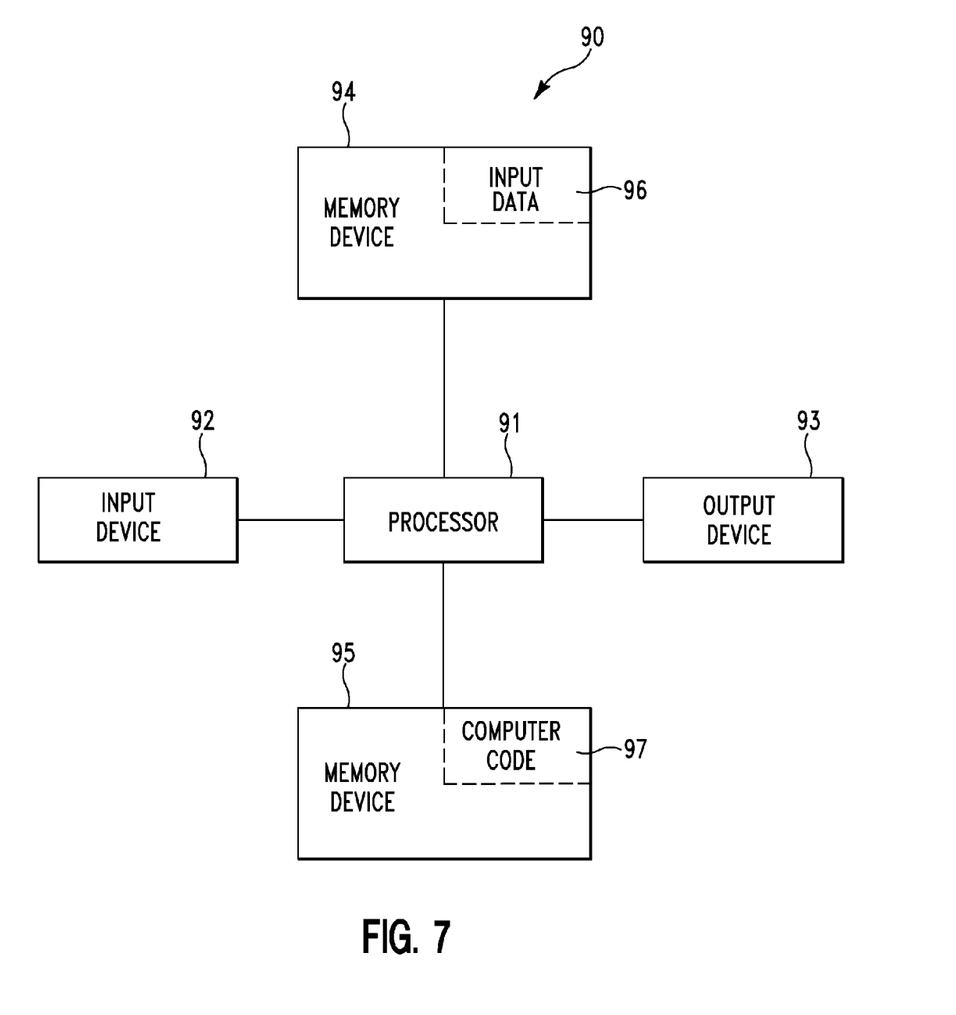
FIG. 7 illustrates a computer system used by or comprised by the system of FIG. 1 for automatically sensing a body portion and automatically delivering an associated therapy, in accordance with embodiments of the present invention.

FIG. 7 illustrates a computer system 90 used by or comprised by the system of FIG. 1 for automatically sensing a body part and automatically delivering an associated therapy, in accordance with embodiments of the present invention. The computer system 90 illustrated in FIG. 6 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithms of FIGS. 2, 4, and 6) for automatically sensing a body part and automatically delivering an associated therapy. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 6) may include the algorithms of FIGS. 2, 4, and 6 and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

While FIG. 7 shows the computer system 90 as a particular configuration of hardware and software, any configuration of hardware and software, as would be known to a person of ordinary skill in the art, may be utilized for the purposes stated supra in conjunction with the particular computer system 90 of FIG. 7. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method for enabling delivery of a specified therapy type to a specified body part of mammal, over specified periods of time, said method comprising for each specified period of time:
    receiving, by a processor of a computing system from physical sensors of a plurality of physical sensors spatially distributed on or in a substrate, a value of an environmental parameter measured by said physical sensors while the mammal is on or in contact with a substrate and in contact with a first subset of the plurality of physical sensors, leaving a remaining subset of the plurality of physical sensors not in contact with the mammal;
    determining, by the processor, a second subset of the plurality of physical sensors as being those physical sensors whose received value differs from a corresponding predetermined reference value, of the environmental parameter by at least a predetermined threshold value, specific to said plurality of physical sensors;
    determining, by the processor, a physical part subset of the second subset, said physical part subset corresponding to the specified body part, said determining the physical part subset comprising utilizing the second subset and virtual data for identifying a plurality of virtual sensors representing the plurality of physical sensors and spatially distributed in virtual subsets to map a space occupied by the mammal's body parts, wherein each subset of the virtual subsets comprises a virtual representation of a differing body part of said mammal's body parts, and wherein said utilizing comprises;
        overlaying the virtual sensors over data retrieved from the second subset; and
        determining, based on results of the overlaying, a virtual part subset of the plurality of virtual sensors corresponding to the specified body part;
    determining based on a cross referencing process, by the processor from the physical part subset, an associated therapy device of a group of therapy devices spatially distributed on or in the substrate, wherein the associated therapy device is positioned in sufficiently close proximity to the specified body part to effectively deliver the specified therapy type to the specified body part;
    generating, by the processor, a control signal comprising instructions to deliver the specified therapy type to the specified body part;
    transmitting, by the processor, the control signal to the associated therapy device to activate the associated therapy device to deliver the specified therapy type to the specified body part; and
    after said transmitting, if said each specified period of time has elapsed then terminating said method, otherwise repeating said receiving, said determining said second subset, said determining said physical part subset, said determining said associated therapy device, said generating, and said transmitting.

2. The method of claim 1, wherein the plurality of virtual sensors comprise torso virtual sensors corresponding to a torso of the mammal, and wherein said overlaying comprises:
    mapping the torso virtual sensors to the second subset of physical sensors;
    determining, based on results of the mapping, a torso subset of the second subset of physical sensors corresponding to the torso of the mammal; and
    using the torso subset of the physical sensors and the virtual part subset to determine the physical part subset.

3. The method of claim 2, wherein the method comprises determining that the specified body part is within the torso of the mammal, and wherein said utilizing comprises:
    mapping the virtual part subset to the torso subset to determine the physical part subset.

4. The method of claim 2, wherein the method comprises determining that the specified body part is external to the torso of the mammal, and wherein said utilizing further comprises:
    determining a set of exterior virtual sensors of the plurality of virtual sensors corresponding to an exterior body part of the mammal attached to the mammal at a point of attachment on the torso, wherein the set of exterior virtual sensors includes the virtual part subset and comprises an attachment sensor coinciding with an attachment sensor of the torso virtual sensors corresponding to the point of attachment;
    determining an attachment sensor of the torso subset of the physical sensors corresponding to the attachment sensor of the torso virtual sensors;
    determining an exterior subset of the physical sensors by mapping the set of exterior virtual sensors to the second subset in a manner that constrains the attachment sensor of the set of exterior virtual sensors to coincide with the attachment sensor of the torso subset of the physical sensors; and
    mapping the virtual part subset to the exterior subset of the physical sensors to determine the physical part subset.

5. The method of claim 1, further comprising:
    receiving, by the processor, said instructions from a source external to the computing system.

6. The method of claim 1, further comprising:
    generating, by the processor based on the value of the environmental parameter, the instructions, wherein the instructions comprise a command selected from the group consisting of a duration for delivering the specified therapy, a frequency for delivering the specified therapy, and an intensity for delivering the specified therapy.

7. The method of claim 1, further comprising:
    determining, by the processor, an additional physical part subset of the second subset, said additional physical part subset corresponding to an additional body part;
    determining, by the processor from the additional physical part subset, a second therapy device of the group of therapy devices spatially distributed on or in the substrate, wherein the second therapy device is positioned in sufficiently close proximity to the additional body part to effectively deliver an additional therapy type to the additional body part;
    generating, by the processor, an additional control signal comprising additional instructions to deliver the additional therapy type to the additional body part; and transmitting, by the processor, the additional control signal to the second therapy device to activate the second therapy device to deliver the additional therapy type to the additional body part.

8. The method of claim 7, wherein said transmitting the control signal and said transmitting the additional control signal are performed simultaneously such that the at least one therapy device and the second therapy device are activated to deliver the specified therapy type and the additional therapy type simultaneously.

9. The method of claim 1, wherein said physical sensors and the associated therapy device are comprised by a networked electronically addressable matrix of said plurality of sensors and a plurality of therapy devices operatively integrated into said substrate.

10. The method of claim 1, wherein said environmental parameters comprise biological parameters selected from the group consisting of respiration rates, temperature, pulse rates, moisture attributes, acceleration, resistance, stress levels, pressure, blood oxygenation, odor, brain waves, metabolic activity, blood chemicals, and electrical activity.

11. The method of claim 1, wherein said substrate is positioned in sufficiently close proximity of an apparatus selected from the group consisting of a bed, a mattress, a chair or seat, a couch, a crib, and a garment.

12. The method of claim 1, further comprising:
determining, by said processor executing logic functions with respect to input data from said plurality of physical sensors, an attribute of an electronically controllable physical characteristic of an electronically adjustable bed or mattress, wherein the attribute is selected from the group consisting of a temperature, a stiffness, a position of an adjustable component, and motion.

13. The method of claim 1, wherein said specified therapy type is selected from the group consisting of magnetic therapy, light therapy, infrared therapy, laser therapy, temperature-based therapy, shockwave therapy, ultrasound therapy, acoustic therapy, vibration therapy, massage therapy, electronic therapy, chemical therapy, electromagnetic therapy, and electromechanical therapy.

14. The method of claim 1, further comprising:
receiving, by said processor, input data associated with said specified therapy type from a a network selected from the group consisting of a home network, a wireless network, a hospital network, and the Internet; and
transmitting, by said processor, output data associated with said specified therapy type to a network selected from the group consisting of a home network, a wireless network, a hospital network, and the Internet.

15. The method of claim 1, wherein said instructions comprise a command for waking said mammal from a sleep cycle in response to a sensed reading from said one of said plurality of physical sensors.

16. The method of claim 1, further comprising:
communicatively coupling said processor to a database comprising clinical conditions mapped to specified sensor readings associated with said plurality of physical sensors.

17. The method of claim 1, further comprising:
programming, by a user executing said processor, said specified therapy type, wherein said specified therapy type is associated with a body portion type of said specified body part, and wherein said programming may be enabled from an input device of said computing system or a remote mobile authorized to interface with and direct activity of a computing system comprising said processor.

18. A computer program product, comprising a computer readable hardware storage device storing a computer readable program code, said computer readable program code comprising an algorithm that when executed by a computer processor of a computing system implements a method, said method comprising:
receiving, by said processor from physical sensors of a plurality of physical sensors spatially distributed on or in a substrate, a value of an environmental parameter measured by said physical sensors while the mammal is on or in contact with a substrate and in contact with a first subset of the plurality of physical sensors, leaving a remaining subset of the plurality of physical sensors not in contact with the mammal;
determining, by the processor, a second subset of the plurality of physical sensors as being those physical sensors whose received value differs from a corresponding predetermined reference value, of the environmental parameter by at least a predetermined threshold value, specific to said plurality of physical sensors;
determining, by the processor, a physical part subset of the second subset, said physical part subset corresponding to the specified body part, said determining the physical part subset comprising utilizing the second subset and virtual data for identifying a plurality of virtual sensors representing the plurality of physical sensors and spatially distributed in virtual subsets to map a space occupied by the mammal's body parts, wherein each subset of the virtual subsets comprises a virtual representation of a differing body part of said mammal's body parts, and wherein said utilizing comprises;
overlaying the virtual sensors over data retrieved from the second subset; and
determining, based on results of the overlaying, a virtual part subset of the plurality of virtual sensors corresponding to the specified body part;
determining based on a cross referencing process, by the processor from the physical part subset, an associated therapy device of a group of therapy devices spatially distributed on or in the substrate, wherein the associated therapy device is positioned in sufficiently close proximity to the specified body part to effectively deliver the specified therapy type to the specified body part;
generating, by the processor, a control signal comprising instructions to deliver the specified therapy type to the specified body part;
transmitting, by the processor, the control signal to the associated therapy device to activate the associated therapy device to deliver the specified therapy type to the specified body part; and
after said transmitting, if said each specified period of time has elapsed then terminating said method, otherwise repeating said receiving, said determining said second subset, said determining said physical part subset, said determining said associated therapy device, said generating, and said transmitting.

19. A method for enabling delivery of a specified therapy type to a specified body part of mammal, over specified periods of time, said method comprising for each specified period of time:
receiving, by a processor from a subset of physical sensors of a plurality of physical sensors spatially distributed on or in a substrate, tag data identifying a tag attached to said specified body part while the mammal is on or in contact with a substrate;
determining, by the processor, a second subset of the plurality of physical sensors as being those physical sensors whose received value differs from a corresponding predetermined reference value, of the environmental parameter by at least a predetermined threshold value, specific to said plurality of physical sensors;

determining, by the processor, a physical part subset of the second subset, said physical part subset corresponding to the specified body part, said determining the physical part subset comprising utilizing the second subset and virtual data for identifying a plurality of virtual sensors representing the plurality of physical sensors and spatially distributed in virtual subsets to map a space occupied by the mammal's body parts, wherein each subset of the virtual subsets comprises a virtual representation of a differing body part of said mammal's body parts, and wherein said utilizing comprises;

overlaying the virtual sensors over data retrieved from the second subset; and determining, based on results of the overlaying, a virtual part subset of the plurality of virtual sensors corresponding to the specified body part;

determining based on a cross referencing process, by the processor from the physical part subset, an associated therapy device of a group of therapy devices spatially distributed on or in the substrate, wherein the associated therapy device is positioned in sufficiently close proximity to the specified body part to effectively deliver the specified therapy type to the specified body part;

generating, by the processor, a control signal comprising instructions to deliver the specified therapy type to the specified body part;

transmitting, by the processor, the control signal to the associated therapy device to activate the associated therapy device to deliver the specified therapy type to the specified body part; and after said transmitting, if said each specified period of time has elapsed then terminating said method, otherwise repeating said receiving, said determining said second subset, said determining said physical part subset, said determining said associated therapy device, said generating, and said transmitting.

* * * * *

UNITED STATES PATENT AND TRADEMARK OFFICE
CERTIFICATE OF CORRECTION

PATENT NO. : 9,005,101 B1
APPLICATION NO. : 14/461862
DATED : April 14, 2015
INVENTOR(S) : Julian Van Erlach It is certified that error appears in the above-identified patent and that said Letters Patent is hereby corrected as shown below:

In the Claims

In Column 15, Line 44 replace the ";" after the word comprises with ":"

In Column 18, Line 31 replace the ";" after the word comprises with ":"

In Column 19, Line 16 replace the ";" after the word comprises with ":"

Signed and Sealed this
Eleventh Day of August, 2015

Michelle K. Lee
*Director of the United States Patent and Trademark Office*